US012802377B2

(12) United States Patent
El Beheiry et al.

(10) Patent No.: US 12,802,377 B2
(45) **Date of Patent: *Nov. 17, 2026**

(54) METHOD FOR VISUALIZING AT LEAST A ZONE OF AN OBJECT IN AT LEAST ONE INTERFACE

(71) Applicant: INSTITUT PASTEUR, Paris (FR)

(72) Inventors: Mohamed El Beheiry, Paris (FR); Jean-Baptiste Masson, Paris (FR)

(73) Assignee: INSTITUT PASTEUR, Paris (FR)

( * ) Notice: Subject to any disclaimer, the term of this patent is extended or adjusted under 35 U.S.C. 154(b) by 156 days.

This patent is subject to a terminal disclaimer.

(21) Appl. No.: 18/897,644

(22) Filed: Sep. 26, 2024

(65) Prior Publication Data

US 2025/0014299 A1 Jan. 9, 2025

Related U.S. Application Data

(62) Division of application No. 17/999,778, filed as application No. PCT/EP2022/056779 on Mar. 16, 2022, now Pat. No. 12,136,181.

(30) Foreign Application Priority Data

Mar. 18, 2021 (EP) .................................... 21305330

(51) Int. Cl.
*G06T 19/20* (2011.01)
*G06T 7/00* (2017.01)
(Continued)

(52) U.S. Cl.
CPC ............ *G06T 19/20* (2013.01); *G06T 7/0012* (2013.01); *G06T 7/62* (2017.01); *G06T 7/90* (2017.01);
(Continued)

(58) Field of Classification Search
None
See application file for complete search history.

(56) References Cited

U.S. PATENT DOCUMENTS

| | | | | |
|---|---|---|---|---|
| 6,771,262 B2 * | 8/2004 | Krishnan | .................. | G06T 7/12<br>600/407 |
| 10,062,200 B2 * | 8/2018 | Sebok | ..................... | G06T 15/08 |

(Continued)

FOREIGN PATENT DOCUMENTS

| | | |
|---|---|---|
| EP | 3076371 A1 | 5/2016 |
| EP | 3493161 A2 | 5/2019 |

OTHER PUBLICATIONS

El Beheiry et al. DIVA: Natural Navigation Inside 3D Images Using Virtual Reality. Journal of Molecular Biology, 2020, 432(16), 4745-4749.

*Primary Examiner* — Kent W Chang
*Assistant Examiner* — Jonathan M Cofino
(74) *Attorney, Agent, or Firm* — NIXON & VANDERHYE

(57) ABSTRACT

The invention concerns a method implemented by computer means for visualizing at least a zone of an object in at least one interface, said method comprising the following steps: obtaining at least one image of said zone, said image comprising at least one channel, said image being a 2-dimensional or 3-dimensional image comprising pixels or voxels, a value being associated to each channel of each pixel or voxel of said image, a representation of said image being displayed in the interface, obtaining at least one annotation from a user, said annotation defining a group of selected pixels or voxels of said image, calculating a transfer function based on said selected pixels or voxels and applying said transfer function to the values of each channel of the image, updating said representation of the image in the
(Continued)

interface, in which the colour and the transparency of the pixels or voxels of said representation are dependent on the transfer function.

20 Claims, 4 Drawing Sheets

(51) Int. Cl.

| | |
|---|---|
| ***G06T 7/62*** | (2017.01) |
| ***G06T 7/90*** | (2017.01) |
| ***G06T 11/10*** | (2026.01) |
| ***G16H 30/40*** | (2018.01) |

(52) U.S. Cl.
CPC ............. *G06T 11/10* (2026.01); *G16H 30/40* (2018.01); *G06T 2200/04* (2013.01); *G06T 2200/24* (2013.01); *G06T 2207/20081* (2013.01); *G06T 2207/20101* (2013.01); *G06T 2207/30096* (2013.01); *G06T 2210/22* (2013.01); *G06T 2210/41* (2013.01); *G06T 2210/62* (2013.01); *G06T 2219/004* (2013.01); *G06T 2219/2012* (2013.01)

(56) References Cited

U.S. PATENT DOCUMENTS

| | | | | |
|---|---|---|---|---|
| 10,593,099 | B2 * | 3/2020 | Sudarsky ................ | G06T 15/08 |
| 2001/0055016 | A1 * | 12/2001 | Krishnan ................ | G06T 15/08<br>345/424 |
| 2004/0070584 | A1 * | 4/2004 | Pyo ......................... | G06T 19/00<br>345/419 |
| 2007/0127791 | A1 * | 6/2007 | Ernvik ................... | G16H 50/50<br>382/128 |
| 2016/0292912 | A1 * | 10/2016 | Sebok ................. | G06F 3/04815 |
| 2019/0147639 | A1 * | 5/2019 | Sudarsky ................ | G06T 15/08<br>345/424 |

* cited by examiner

METHOD FOR VISUALIZING AT LEAST A ZONE OF AN OBJECT IN AT LEAST ONE INTERFACE

CROSS-REFERENCE TO RELATED APPLICATIONS

This application is a divisional of U.S. patent application Ser. No. 17/999,778 filed on Nov. 23, 2022, which is the U.S. National Stage of International Application No. PCT/EP2022/056779 filed on Mar. 16, 2022, which claims the benefit of EP application Ser. No. 21/305,330.9 filed on Mar. 18, 2021, all of which are incorporated herein by reference.

FIELD OF THE INVENTION

The invention relates to a method for visualizing at least a zone of an object, more particularly for visualizing at least a zone of a patient, in at least one interface.

BACKGROUND OF THE INVENTION

Medicine takes advantage of medical imaging techniques to generate images of the interior of a patient body for clinical analysis and medical intervention, as well as visual representation of some organs or tissues. Medical imaging aims to reveal internal structures of the body hidden for example by the skin and bones, in order to diagnose and treat diseases or to prepare any surgery.

Medical images, generated for example by Computed Tomography (CT), Magnetic Resonance Imaging (MRI), Positron Emission Tomography (PET) or Ultrasounds can be 2-dimensional (2D) or 3-dimensional (3D) images. A 3D image can be computed from a stack of 2D images or obtained directly.

Each image comprises pixels (for 2D image) or voxels (for 3D image), a value being associated to each channel of each pixel or voxel of said image. An image may comprise only one channel, in the case of a monochromatic image for example. On the contrary, an image may comprise multiple channels, for example one for each primary colour (red, green, blue), in the case of colour image. The terms voxels and pixels may be used, by extension or analogy, to any of the 2D or 3D images.

2D medical images are often slice-based representations that allow radiologists to perform diagnoses, measure structures of interest and assess treatment strategies. Surgeons, however, benefit from detailed, to-scale representations of patients as “avatars” or “digital twins” in a natural 3D viewing context such as that provided by virtual and augmented reality immersive visualization technologies.

Volume rendering of 3D medical images is often used in several healthcare contexts, but the quality of the rendered image along with the contrast between anatomical structures of interest strongly depends on the type of transfer function that is applied to the image.

A transfer function applied to an image aims to modify the representation or rendering of said image, by modifying the colour (i.e. an emission characteristic) and the transparency (also called opacity, i.e. an absorption characteristic) of the pixels or voxels of said representation.

Conventional software allow users to apply pre-defined transfer functions, which attribute optical properties to the pixels or voxels. Such pre-defined transfer functions are not always adapted to corresponding analysis.

Manual adjustments of some hyper-parameters of the transfer functions are sometimes allowed by the software. However, manual design of said transfer function can be a tedious and time consuming task and does not necessary lead to the best optimization of the transfer function for the concerned case.

There is also a need for facilitating the communication between medical specialists using different interfaces. In particular, radiologists are trained to use 2D viewing interface whereas surgeons are using a 3D interface which accurately resembles the patient in the operating room. Such interaction could benefit from both expertise for facilitating diseases diagnosis or surgery preparation.

BRIEF SUMMARY OF THE INVENTION

To these aims, the invention proposes a method implemented by computer means for visualizing at least a zone of an object in at least one interface, said method comprising the following steps:

- obtaining at least one image of said zone, said image comprising at least one channel, said image being a 2-dimensional or 3-dimensional image comprising pixels or voxels, a value being associated to each channel of each pixel or voxel of said image, a representation of said image being displayed in the interface,
- obtaining at least one annotation from a user, said annotation defining a group of selected pixels or voxels of said image,
- calculating a transfer function based on said selected pixels or voxels and applying said transfer function to the values of each channel of the image,
- updating said representation of the image in the interface, in which the colour and the transparency of the pixels or voxels of said representation are dependent on the transfer function.

BRIEF DESCRIPTION OF DRAWINGS

Other features, details and advantages will be shown in the following detailed description and on the figures, on which.

DETAILED DESCRIPTION OF INVENTION

Figure 1:
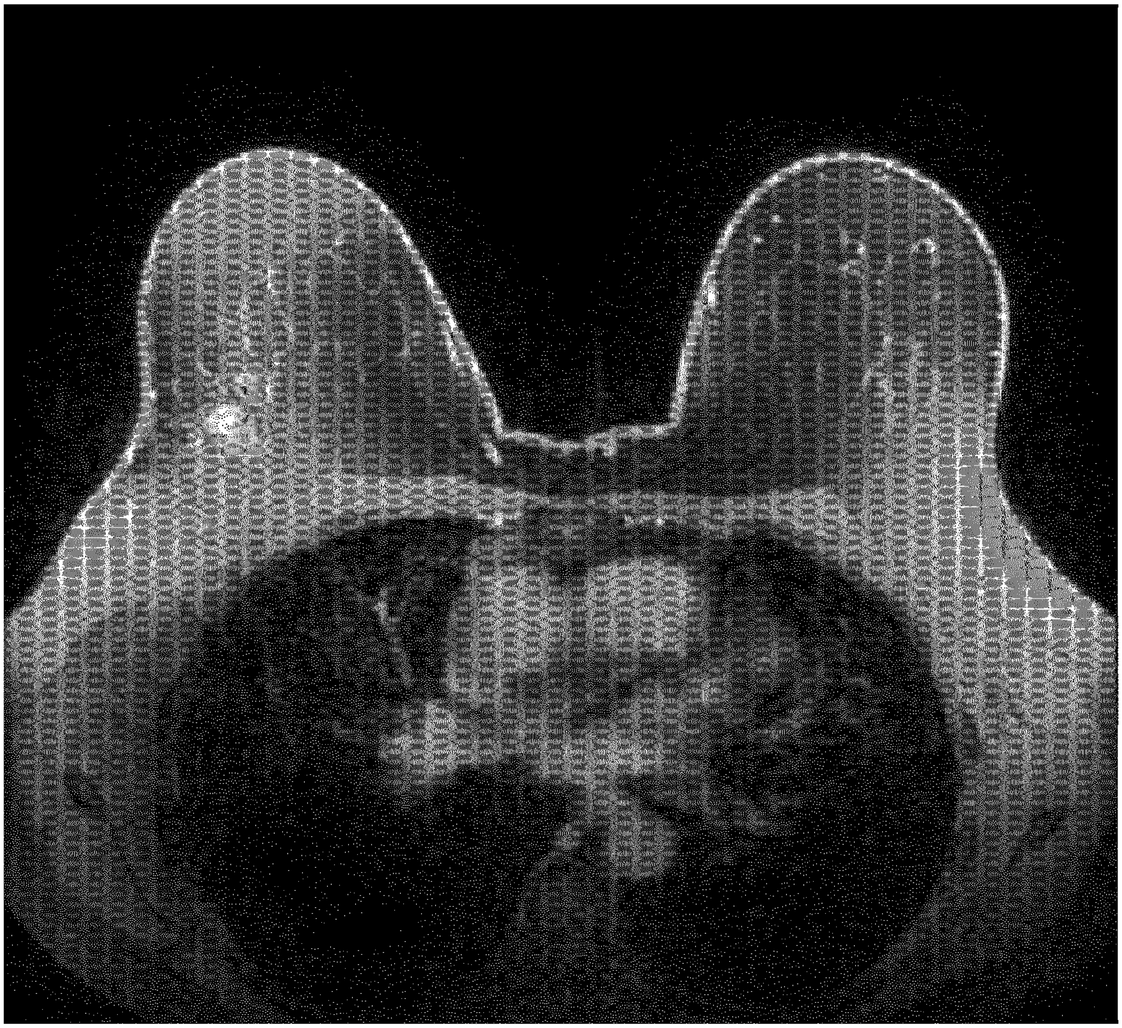
FIG. 1 shows an example of the first interface showing a 2D representation of a 2D image prior to the selection of pixels or voxels through annotations.

The invention is applicable to medical image as well as to other types of images. The invention is not limited to visualizing at least a zone of patient body.

Contrarily to the prior art, in the case of the invention, the transfer function is not predefined or modified only by manually fine-tuning the hyper-parameters of said transfer function. Indeed, in the invention, annotations of the image are used to adapt the transfer function and thus the resulting representation of the image. Such process is called semi-automatic definition or parametrization of the transfer function.

Such ergonomic and dynamic modification of the transfer function is particularly efficient to quickly and optimally modify the transfer function on the basis of the content of the image.

The interface may be a graphical user interface (GUI). The user may interact with the interface through at least one controller, for example a mouse, a keyboard and/or a virtual reality controller.

Said method may comprises the following steps:

- obtaining at least one 2-dimensional or 2D image of said zone, said 2D image comprising pixels and at least one channel, a value being associated to each channel of each pixel of said 2-dimensional image, a representation of said 2D image being displayed in a first interface,
- obtaining at least one 3-dimensional or 3D image of said zone, said 3D image comprising voxels and at least one channel, a value being associated to each channel of each voxel of said 3D image, at least some of the voxels of the 3D image corresponding to some pixels of the 2D image, a representation of said 3D image being displayed in a second interface,
- obtaining at least one annotation from a user, said annotation defining a group of selected pixels of said 2D image or a group of selected voxels of said 3D image,
- propagating the selection of said group of pixels or voxels selected in the 2D or 3D image to the 3D or 2D image, respectively, by selecting the voxels or the pixels of said 3D or 2D image that corresponds to the selected pixels or voxels of said 2D or 3D image, respectively,
- calculating a first transfer function based on said selected pixels of said 2D image and applying said first transfer function to the values of each channel of the 2D image,
- updating the representation of the 2D image in the first interface, in which the colour and the transparency of the pixels of said representation are dependent on the first transfer function,
- calculating a second transfer function based on said selected voxels of said 3D image and applying said second transfer function to the values of each channel of the 3D image,
- updating the representation of the 3D image in the second interface, in which the colour and the transparency of the voxels of said representation are dependent on the second transfer function.

According to these features, the first interface and the representation of the 2D image (or 2D representation) can be adapted to the needs of a first user, for example a radiologist, and the second interface and the representation of the 3D image (or 3D representation) can be adapted to the needs of a second user, for example a surgeon.

In this manner, an element to be detected that could possibly go unseen on one of the 2D or 3D representations would have a better chance of being detected on the other representation. This double verification using the both the 2D and 3D interfaces thus improves the detection. Of course, the same user can use both first and second interfaces in order to visualize and interact with both 2D and 3D representations.

The propagation of the group of selected pixels or voxels from one image to another allows a dynamic and simultaneous adaptation of the first and the second transfer function. In other words, annotations on one interface have an effect on the representations of the images on both interfaces.

Moreover, according to the above-mentioned features, an annotation (for example a region of interest) is transferred from one interface to another. However, the transfer function is not transferred, this transfer function being recalculated at each annotation of the user and for each interface. This allows to obtain in an interactive and dynamic way the best transfer function for each of the 2D and 3D interfaces.

Such behaviour facilitates interactions between interfaces, for example between two users.

The group of selected pixels or voxels of the corresponding image may be updated by obtaining at least one additional annotation from a user through at least one interface.

In other words, the updates of the representations of the images on both interfaces can be an interactive process where each successive annotation has an effect on said representations.

A group of pixels may be selected in the 2D interface or first interface and a group of voxels may be selected in the 3D or second interface, the union of corresponding pixels and voxels selected in both interfaces may be used to calculate the corresponding first and second transfer functions.

In this context, if the initial transfer function parameterization is not optimal, annotations positions can be readjusted, in either the first or second interface, and the transfer function re-parameterized allowing for a convergence towards the optimal image representation.

Said annotations may concern adding or removing pixels or voxels from the group of selected pixels or voxels.

More particularly, some pixels or voxels may be added through annotations in one interface whereas some pixels or voxels previously added may be removed through annotations in the other interface.

At least one of the transfer functions may be calculated according to the following steps:

- selecting a first and a second domain of interest A and B, each domain comprising a group of pixels or voxels based on said selected pixels,
- creating a first feature tensor and a second feature tensor on the basis of pixels or voxels of the first and second domains of interest A and B, respectively,
- defining a statistical test that would differentiate the first domain A from the second domain B through the optimal Maximum Mean Discrepancy (MMD) of the statistics of features associated to the first domain A and the second domain B,
- defining, for each pixel or voxel of the image, the colour C of said pixel or voxel with the following equation:

$$C(v) = \frac{f^*(v) - \min(f^*(v))}{\max(f^*(v)) - \min(f^*(v))}$$

- where f*(v) is the witness function of the value of the pixel or voxel v, defined by $$f^*(v) \propto \mu_P - \mu_Q = \frac{1}{m}\sum_{i=1}^{m} k(x_i, v) - \frac{1}{n}\sum_{j=1}^{n} k(y_j, v)$$

where k is a kernel defining a value representative of the distance between the features associated to pixel or voxel xi belonging to domain A and yj and the features associated to the pixel or voxel v, with m the number of pixel or voxel in A and n the number of pixel or voxel in domain B defining for each pixel or voxel of the image, the transparency T of said pixel or voxel with the following equation:

$$T(v) = \frac{h_A(v) + h_B(v)}{Z_{A,B}}$$

where:

$h_A(v)=(k*\rho)(v)$ is the smoothed density, convolution of the kernel with the density of features, of the features associated to voxel v of the first domain A with the kernel k, $h_B(v)=(k*\rho)(v)$ is the smoothed density, convolution of the kernel with the density of features, of the features associated to voxel v of the second domain B with the kernel k, and $Z_{A,B}$ is a normalising constant ensuring that $\max(Z_{A,B})=c$ with $c\leq 1$ a predetermined constant defining the maximal transparency factor.

Said method for calculating the transfer function requires little computing power and is suitable for a large number of applications.

At least one of the transfer function may be calculated according to the following steps:

selecting a first and a second domain of interest A and B, each domain comprising a group of pixels or voxels based on said selected pixels, creating a first feature tensor and a second feature tensor on the basis of the first and second domains of interest A and B, respectively, sample pixels or voxels in the first and second domains of interest A and B to have $$n_A^* = n_B^* \text{ and } 2n_A \leq n_{max},$$

where $n_A$ is the number of sample pixels or voxels in the first domain A and $n_B$ is the number of sample pixels or voxels in the second domain B and where $n_{max}$ is a predetermined value, defining, for each pixel or voxel of the image, the colour C of said pixel or voxel $$C(v) = \frac{f^*(v) - \min(f^*(v))}{\max(f^*(v)) - \min(f^*(v))}$$

with $f^*(v)=(\beta p_A(v)+1)g(v)$ as the normalized product of the shifted probability for said pixel or voxel to belong to domain A by the value of one feature, g (v) of said pixel or voxel v. β is a predefined constant.

defining for each pixel or voxel of the image, the transparency T of said pixel or voxel with the following equation:

$$T(v) = \frac{h_A(v) + h_B(v)}{z_{A,B}}$$

where:

$h_A(v)=(k*\rho)(v)$ is the smoothed density, convolution of the kernel with the density of features, of the features associated to voxel v of the first domain A with the kernel k, $h_B(v)=(k*\rho)(v)$ is the smoothed density, convolution of the kernel with the density of features, of the features associated to voxel v of the second domain B with the kernel k, and $Z_{A,B}$ is a normalising constant ensuring that $\max(Z_{A,B})=c$ with $c\leq 1$ a predetermined constant defining the maximal transparency factor.

Said method for calculating the transfer function offers performances that allows a user to better identify portions of interest in the representation, even when such identification appears particularly difficult or ambiguous on the 2D or 3D image.

The first domain of interest may be defined as the group of selected pixels or voxels based on the annotation.

The second domain of interest may be automatically defined as another group of pixels or voxels that does not contain the pixels or the voxels of the group of selected pixels or voxels based on the annotation.

Alternatively, the second domain of interest may be defined as another group of pixels or voxels that are selected by the user, based on a complementary annotation.

Each feature tensor may define, for each pixel of the corresponding domain of interest, at least one feature value selected from the following list of features:

the value of the pixel or voxel v, $\nabla_l v$ the regularised gradient (over scale l) of the pixel or voxel values, regularisation is performed by Gaussian convolution $\nabla_l v=\nabla(\mathcal{N}_l * I)$ with $\mathcal{N}$ the Gaussian of null averaged value and standard deviation of l and I is the image stack, $S_l(v)$ the entropy of a patch of size l around pixel or voxel v, $d(v)=(\mathcal{N}_{l_1} * I)(v)-(\mathcal{N}_{l_2} * I)(v)$ difference of convoluted images at pixel or voxel υ, where $(l_1, l_2)$ are the two scales associated to the Gaussian I is the image stack, $\sigma_l(v)$ the standard deviation of the patch of size l centred on pixel or voxel v, $KL_{l,m}(v)$ the Kullback-Liebler distance between the patch of size l and the surrounding patch of size l+m centred on pixel or voxel v, $\tilde{\mu}_l(v)$ the median values of the voxels in the patch of size l centred on pixel or voxel v, $\nabla \log(\mathcal{N}_l * I)$ the logarithmic derivative of the convolved image at pixel or voxel v, $d_{p\text{-}UMAP,l,m}(v)$ the low dimensional euclidean distance in the latent space generate by a parametric UMAP for a patch of size l and the surrounding patch of size l+m centred on pixel or voxel v. This feature is used on specialised solutions where a database of medical images has been assembled. A parametric UMAP has been trained on a predefined set of patches size on 2D image slices in the 3 main axes (Sagittal, Coronal and Axial). The training has been done to reduce the dimension of the patch to a 2D latent space. When evaluating the distance l and l+m are approximated as the closest value used for training.

$(r, \theta)_{p\text{-}UMAP}(v)$ the polar coordinates of the pixel or voxel v on the latent space generate by a parametric UMAP centres on pixel or voxel v, $S_{p\text{-}UMAP,l}(v)$ the convex hull surface of the domain of size l around pixel v Said kernel k may be selected from the following list of kernels:

$$-k_G(x, x') = \sigma^2 \exp\left(-\frac{(x-x')^2}{2l^2}\right),$$

$$-k_{Per}(x, x') = \sigma^2 \exp\left(-2\frac{\sin^2\left(\frac{\pi(x-x')}{p}\right)}{l^2}\right),$$

$$-k_{lin}(x, x') = \sigma_b^2 + \sigma_v^2(x-l)(x'-l)$$

$$-k_{cau}(x, x') = \sigma^2\left(1 + \frac{(x-x')^2}{2\alpha l^2}\right)^{-\alpha}$$

$$-k_{exp}(x, x') = \exp\left(-\left(\frac{r}{l}\right)^{\gamma}\right)$$

where:

x and x' are features of the corresponding pixels or voxels, vectors of size up to 8, $\{\sigma, l, p, \sigma_b, \sigma_v, \alpha, \gamma\}$ are hyper-parameters of the kernels, these parameters being predefined, or set automatically or by the user.

The above mentioned hyper-parameters may be modified or set by at least one user through at least one interface.

A same medical image or medical image series can be used for obtaining a slice-based 2D image and a 3D image according to the invention.

Said medical image series may be a Digital Imaging and Communications in Medicine (DICOM) image series.

The representation of the 3D image may be obtained through volume ray casting methods.

The first interface may be displayed on a computer screen.

The second interface may be displayed on a computer screen and/or on a display of a virtual reality (VR) device. Said VR device may comprise a stereoscopic, motion-tracked head mounted display and a VR controller. Such VR device allows a natural 3D visualization and interaction with the representation of the 3D image.

The above mentioned semi-automatic transfer function definition or parametrization process is compatible with additional manual options. A user may also interact with the transfer function and/or add or remove portions of the transfer function. The user may modify the shape of the transfer function in a feature space of the transfer function and may substitute the function optimised by a custom function. All parameters associated to the optimised transfer function may be accessible.

In this manual situation, a user may determine the transparency and the colour characteristics of the transfer function manually, for example in a specialized interface or specialized area of the first or second interface. This interface or area consists of an interactable absorption curve and a corresponding colour mapping.

The simplest form of transfer function is the one-dimensional version, which associates an opacity and colour based on the pixel intensity value. Critical to this transfer function is the smoothness in opacity and colour variance between pixel intensity values. Consequently a one-dimensional spline or gaussian profile may be used to transition between colours and a variety of function to define opacities.

A 1D interface or area (in this case D refers to the dimension of the transfer function) may allow building the transfer function either using an user controlled spline, or a set of predefined template functions including Gaussian, asymmetric Gaussian, log-normal, Gaussian mixture etc. Transparency and colour may be rendered independently.

While appropriate in many cases, such simple one-dimensional descriptions of the transfer function can give rise to concerns, especially in highly heterogeneous medical data. Effectively, one-dimensional transfer functions such as those described above cannot distinguish between different parts of the volume data if they happen to have the same raw pixel or voxel intensity value.

For this reason, two-dimensional transfer functions may be used, such transfer function considering both the data value (pixel or voxel value) and the gradient magnitude. This approach allows to see interfaces between parts of the volume (e.g. between bone and tissue) and also better distinguishes homogeneous regions.

The most common form of two-dimensional transfer function is one that relates the pixel or voxel intensity to the gradient magnitude (i.e. first derivative of the pixel or voxel intensity) or laplacian (i.e. second-derivative of the pixel or voxel intensity). In the case of CT images, for example, these types of transfer functions are particularly useful for isolating tissues such as skin and bone. Interfaces between homogeneous regions in this type of transfer function appear as arcs in the corresponding two-dimensional histogram. This permits a more complete isolation (not segmentation) of structures in the image as the gradient or laplacian is an additional parameter to the pixel or voxel intensity to optimize representations.

A 2D interface or area may allow building the transfer function in a similar fashion as the 1D interface or area with a more complex dictionary. The interface or area may allow the combined use of shape, functions and geometric delimitation to design the transfer function.

According to an embodiment of the invention, a synchronization between the first interface and the second interface may be obtained through at least one manager comprising a set of procedures, classes and message generating programs that interfaces with and synchronizes said interfaces and stores variables controlling visualization-relevant information (e.g. annotations, transfer functions, image transformations) between said user interfaces.

The manager may comprise a data storage holding information in a universal format readable to all user interfaces.

A separate manager may exist for each type of visualization-relevant information. Each manager implements at least one or each of the following generic functions:

- export data from a manager data storage to a format readable outside of an application (e.g. CSV text, PNG image, STL mesh), import data from outside of the application to the manager data storage (e.g. CSV text, PNG image, STL mesh),

- receive data from at least one interface and store said data into the manager data storage and update all other interfaces with a visual readout of this data inclusion,
- remove data from at least one interface and remove said data from the manager data storage and update all other interfaces with a visual readout of this data removal,
- update the visual readout of a given interface with the addition of a new visual element (e.g. a landmark, ruler measurement, volumetric measurement),
- remove the visual readout of a given interface with the removal of an existing visual element (e.g. a landmark, ruler measurement, volumetric measurement).

Each data element stored (e.g. landmark, ruler measurement, volumetric measurement, etc.) may have a unique identifier associated to it which is used to ensure synchronization between each interface.

Data may be entered by users using a mouse or the VR controller in the corresponding 2D or 3D interface. Positional information as well as button presses in either the mouse or the VR controller may be received by an input handler which transcribes them into an action. For example, a user clicking on a specific region in a 2D image slice may lead to an action defined by the creation of a landmark. A user annotating with the mouse may lead to both the creation of annotations in the 2D representation and, through propagation, a corresponding annotation in the 3D representation, and vice versa for annotation creation with the VR controller.

All actions in one interface may have their corresponding actions in the other. Actions may include image transformations such as region cropping, region deletion, orientation adjustments and scaling or zooming. Another type of action may be the addition of annotations to an image such as landmarks, ruler measurements and per-pixel tagging. Similarly, the removal of annotation may constitute an action. An action can correspond to adjustments to the transfer function, which controls the visual characteristics of the 2D representation or 3D representation. That is, adjusting the brightness, colour and transparency of the image as a function of features associated with the pixel or voxel.

After its creation, a visual readout of an action may be effected upon the respective interface in an interface update. For example, an action in the first interface that creates a landmark may render a graphical representation of the landmark in the first interface.

The interface update may be followed by the raising of an event via an event trigger which notifies the manager of the user action.

Interfaces may be perfectly synchronized to ensure data coherency and streamlined communication between both interfaces and their respective users. A means of doing so is through the use of a manager, which may have two main functions. The manager may connect both interfaces via event invocations to ensure that actions in one interface manifest in the other. The creation of an action may raise an event in the respective interface which notifies the manager then handles. The manager may then receive event arguments from the respective interface and perform two operations in sequence. It may first save information stored in the arguments into a centralized internal data storage in a format readable by both interface types. For example, this data may be the position of an annotation or an image transformation. As a second step, the manager may raise an event in the other interface and may send the relevant arguments. These arguments may be received by the interface update unit and may be directly transcribed into the proper graphical elements.

As mentioned above, a manager may be associated to each type of annotation. For example, a manager may deal with adding and removing landmarks and a separate manager may deal with transfer function changes.

Such manager is an optimal means for data coherency, consistency, synchronization and security between multiple user interfaces.

The fact of having all the relevant visual information from the different user interfaces stored in a universal format in a centralized location eliminates conflicts between the data types presented in the respective interface.

The effect of an action (data addition, removal, transformation) in one user interface is immediately represented in every other interface.

Exportation of data is always consistent as annotations from all user interfaces are stored in one centralized location.

Functions requiring access to multiple data types (e.g. the transfer function requiring access to tagged pixel or voxel information) can do so directly by accessing the relevant manager type.

A radiologist may make an annotation in the first interface (the user interface with which they are accustomed) and the exact same annotation will appear represented in 3 dimensions in the second interface for a surgeon to appreciate, so that there is no ambiguity in the annotation being visualized. In addition, a surgeon can make an annotation in the second interface and the same annotation will appear in the first interface. The user navigation of the data of the first interface may be visualized within the second interface in the form of 3 moving 2D planes. The position of the mouse in the first interface may be indicated within the second interface as a highlighted sphere.

The user navigation of the data in the 3D interface may be visualised within the 2D interface in the form of the autonomous movement of the sagittal, axial and coronal planes. The position of the VR controller may be indicated in the form of a moving coloured circle.

More generally, the mouse position or the VR controller position in one interface may be seen immediately in the other interface.

The centralized data feature ensures that the data visualized in the different user interfaces is the correct data. The manager may be tailored to ensure a modular implementation. The manager model may ensure that each visualization-relevant information is accessed with the same interface. Integration of new features may not require changes in the manager. This abstraction makes for a simple implementation of new types of data types to be synchronized across user interfaces.

The manager may use an event trigger to update all interface upon the addition or removal of a visualization-relevant data type in real-time. This ensures instantaneous visualization of data-types across all interfaces.

Annotations may be information that are superimposed onto visual representations. Namely, identical annotations may be represented in either first or second user interfaces. While being identical in precision of position and orientation, their appearance may be tailored to each interface. Below are described some of the annotations that may be added or removed by a user in the corresponding interface.

A landmark is an annotation placed by a user at a specific pixel or voxel location in an image or in a representation. It may be represented by a sphere, flag or arrow.

A ruler annotation is a 2D or 3D distance measurement superimposed onto an image or representation. It is typically represented by a line between the two ends defining the measurement.

A volume annotation is a volume measurement within a 3D image or within a 3D representation. It may be shown by a sphere, ellipsoid or other 3D geometric shape. A volume annotation may also serve as a means to measure the surface area of a region.

A tag is an annotation that represents individual pixel or voxel in an image or representation. It may be shown by a semi-transparent colour that overlays the original pixel or voxel in the image.

A bounding box is an annotation that is used to identify a region or object in an image or representation. It may be shown by a box outline in a 2D image or 2D representation and 3D box in a 3D image or 3D representation.

A path is a spline interpolated curve defined in any of the first and second interface allowing the creation of an automated viewing procedure along it. The path may appear on all interfaces as a coloured line.

Annotations may be used to add position information inside a volumetric image stack and ensure its proper visualization in 2D image or 2D representation and 3D image or 3D representation. Such annotations may contain information concerning the number of tumours (e.g. with landmarks), the size of a tumour (e.g. with the ruler measurement), the volume of a tumour (e.g. via a volumetric annotation), the position of a landmark, the automated or semi-automated segmentation of a structure of interest and a segmented object (surgical instrument, foreign object).

The use of annotations such as landmarks and ruler measurements is a means for the radiologist to communicate clinical information contained in a medical image to the surgeon. Such information can include the size, volume and number of tumours as well as excision margins. Landmarks can also indicate areas of interest such as candidate blood vessels for oncoplastic procedures, the presence of congenital heart defects and the precise position of bone fractures.

The surgeon can annotate the medical image to plan surgical gestures. For example, the location of incision planes can be ascertained with the use of the ruler and tagging tools. For laparascopic procedures, path annotations enable an intuitive visualization of the surgical path.

Tagging and bounding box annotations in the 2D representation or 2D image play a pivotal role in defining the optimal transfer function for the other interface. Effectively, as mentioned above, local information contained in the tagged or bounded region indicate the region of interest (group of pixels or voxels) that can be readily integrated in the transfer function parameterization. An image transformation, as mentioned above, is a geometric edition performed on an image.

Image transformation may comprise image cropping or deletion.

Image cropping involves removing the exterior of a region in an image. A cropped region is typically selected by common geometric shapes such as a square, cube or sphere.

Cropping domains may appear in both first and second interfaces and can be altered from both interfaces. Synchronization of the interface allows the cropping region to move simultaneously on all interfaces.

Image deletion involves removing the interior of a region in an image. A deleted region may typically be selected by common geometric shapes such as a square, cube or sphere.

Image transformations prime the medical images for unencumbered visualization by specialists. With cropping routines, for example, a specific region or organ of interest can be isolated. Deletion routine can allow for removal of regions that are not pertinent to the patient condition or pathology.

Medical images such as MRI and CT-scans typically capture significant image information that is not relevant to the patient condition or pathology. For example, a hepatic CT-scan capture signals for the heart, intestines, lungs and rib cage that can otherwise obscure a desired visualization of the liver. In cropping or deleting irrelevant parts of the image an unobscured medical visualization may be possible in both first and second interfaces.

Moreover, in many situations, images (and more particularly medical images) are multi-channel. For instance, the same zone of the same patient may be imaged multiple times with different acquisition parameters or imaging modalities. Each image of said zone may then constitute a channel of an image. This can be the case of multiple MRI weightings imaged in the same session (e.g., T1, T1-injected, T2, etc.). It can also correspond to the case of the same patient being imaged with an MRI and a CT-scan.

Multimodal image fusion is the act of relating information from these multiple channels to each other.

Image fusion can be performed using channels. Each channel may be associated to a dedicated transfer function.

Channels and multi transfer functions may be handled by the manager.

All image channels may be visualised independently by activating individual channels.

A subset of image channels may be visualised together by activating multiple channels.

The associated transfer functions may be applied to the 3D image in the second interface to obtain the 3D representation.

In the first interface, the multiple image channels may be fused. The practice is however to display only one channel in the first interface.

Annotations performed in one image channel may simultaneously transmitted to all channels of said image. Annotations in one channel can be used to generate transfer functions in all channels. A transfer function defined in one channel can be applied to other channels.

When alignment of the multimodal imaging is not ensured by the recording technology or when the patient morphology was altered between the different imaging, the procedure can be updated using landmarks that can be positioned in the 2D or 3D representation or image in multiple channels, said channels being realigned one to another using such annotations.

Multimodal image fusion is useful for consolidating information contained in different image sequences or modalities together, each sequence or modality defining a channel. Aligning these types of information together leads to an enhanced picture of the patient condition.

A multi-sequence example would include relating the complementary information contained in a T1-weighted MRI to that in a T2-weighted MRI in the context of prostate imaging. In the T2-weighted image, the prostate is typically well delimited. In the T1-weighted image, visualization of treatment effects in relation to blood vessels in particular are depicted. Combining these two information types in a single visualization by using the same annotations may lead to an enhanced understanding on the part of specialists when evaluating a treatment option.

A multi-sequence example can also include relating MRI images for the same patient taken at different times during a treatment. For example, a breast MRI prior to a neoadjuvant treatment can be related post chemotherapy to evaluate the tumour response. Relating these two types of information in the same visualization aid breast cancer surgeons in defining proper tumour excision margins.

A multi-acquisition example would include the fusion of an MRI and a CT-scan sequence. An application in this context would be for assessing infiltration of a tumour in bone tissue. The enhanced tissue contrast MRI allows for a visualization of the tumour while the CT-scan allows for a clear visualization of the bone tissue.

The invention also relates to a computer program, comprising instructions to implement at least a part of the above mentioned method when the software is executed by a processor.

The invention also relates to a computer device comprising:

- input means for receiving at least one image of a zone of an object, a memory for storing at least instructions of the aforesaid computer program, a processor accessing to the memory for reading the aforesaid instructions and executing then the aforesaid method, interface means for displaying the representation of the image obtained by executing said method.

The invention also relates to a computer-readable non-transient recording medium on which a computer software is registered to implement the aforesaid method, when the computer software is executed by a processor.

The invention also relates to a method of generating a 3D model of a patient's anatomical structure of medical interest wherein the method comprises:

implementing by computer means the method for visualizing at least a zone of an object as disclosed herein wherein the object is displayed on a medical 3D-image and is a patient's anatomical structure(s) comprising a zone of medical interest and the medical 3D-image is a magnetic image resonance (MRI) image, a Computed Tomography (CT) scan image, a Positron Emission Tomography (PET) scan image or a numerically processed ultrasound recordings image and displaying a 3D model of the patient's anatomical structure including the zone of medical interest, for example using virtual reality means, preferably a virtual reality headset.

In some embodiments of the method of generating a 3D model, a user provides at least one annotation in the medical 3D-image wherein the at least one annotation selects pixels or voxels in the zone of medical interest to improve visualisation of said zone or/and visualization of the boundaries of the zone of interest and/or the at least one annotation selects pixels or voxels outside the zone of medical interest to enable image transformation by cropping or deletion of interfering structures such as surrounding tissues in the zone of interest, bones, muscles or blood vessels.

In some embodiments, the zone of interest is or encompasses the medical image of a lesion or a group of lesions, a tumor, especially a cancer, or an anatomic abnormality.

The user may be a person, in particular a medical personnel, trained to visualize, annotate and/or interact with data gathered from medical image.

In some embodiments of the method the 3D model is generated using raw 3D image imaging data or alternatively using segmented 3D image data.

The invention accordingly also relates to a method of analyzing a 3D model obtained from of a medical 3D-image previously acquired from a patient in need of determination of his/her condition, disease or health status wherein the method comprises:

implementing by computer means the method for visualizing at least a zone of an object as disclosed herein wherein the object is a patient's anatomical structure(s) displayed on a medical 3D-image and comprising a zone of medical interest and the medical 3D-image is a magnetic image resonance (MRI) image, a Computed Tomography (CT) scan image, a Positron Emission Tomography (PET) scan image or a numerically processed ultrasound recordings image and displaying a 3D model of the patient's anatomical structure including the zone of medical interest;

analyzing the displayed 3D model in particular visualizing, tagging, manipulating and/or measuring metrics based on imaging data of the 3D model, thereby characterizing the patient's anatomical structure in the zone of medical interest.

The invention also concerns a method of diagnosing or monitoring a patient's condition, disease or health status wherein the method comprises:

implementing the method as above disclosed, collecting the data relative to the metrics measured based on imaging data wherein the metrics enable mapping morphological, geometrical or position features of medical interest for the patient's condition, disease or health status.

In some embodiments, the collected data are determinative to conclude on the patient's condition, disease or health status.

In some embodiments the geometrical features encompass volume ratio of the zone of interest, in particular of the lesion(s) or tumor or anatomical abnormalities with respect to the volume of the anatomical structure. In some embodiments the position features of the zone of interest encompass the relative position of the zone with respect to the contours of the anatomical structure or elements constitutive thereof.

In some embodiment the morphological, geometric or position features enable detection or visualization of a multicentric or multifocal zone of interest, in particular of multicentric or multifocal lesions.

In some embodiments the morphological, geometrical or position features are assessed in the natural context of the zone of interest displayed on the 3D model, such as in the presence of represented blood vessels, muscles or other tissues, i.e., without pretreatment of the data displayed. In other embodiments the morphological, geometrical or position features are assessed after image transformation has been performed prior to displaying the 3D model such transformation involving or consisting of cropping or deleting interfering structures such as surrounding tissues in the zone of interest, bones, muscles or blood vessels In some embodiments the methods of the invention are for the detection or monitoring of a zone of interest which is a tumor (including a tumor encompassing multiple lesions) in a patient wherein the visualized or measured metrics are selected in the group of spatial localization of the tumor in the specific organ or in a specific part thereof, determination of the number of lesions, position of the tumor relative to the contours of the affected anatomical structure or body part, in particular of the affected organ, especially determination of the boundaries (margins) of the tumor, determination of the volume of the tumor or of the ratio of volumes respectively of the tumor and of the residency volume of the organ containing it. In a particular embodiment the tumor is a breast cancer.

The methods of the invention may be used for assisting in medical decision relating to a patient's condition disease of health status, for assisting in medical preoperative planning including for assisting in preparing surgery. In particular the methods may be used for applications in radiology, surgery-specific topics, in clinical diagnosis or monitoring of patient's condition or disease. Applications in the field of surgery proved to improve accuracy of medical image visualization and analysis and as a consequence to provide valuable data and information to design or conduct surgical strategy. Accordingly the invention may be applied in the field of cancer treatment, in particular in diagnosing cancer or in planning oncoplastic surgery, in particular in the field of breast cancer treatment by surgery, but also more broadly in the field of treatment of trauma, especially in planning trauma surgery, in the field of treatment of anatomical diseases such as heart diseases in particular affecting cardiac anatomy, in the field of liver diseases. It may also be applied in the field of paediatric surgery or orthopaedic surgery.

Figure 2:
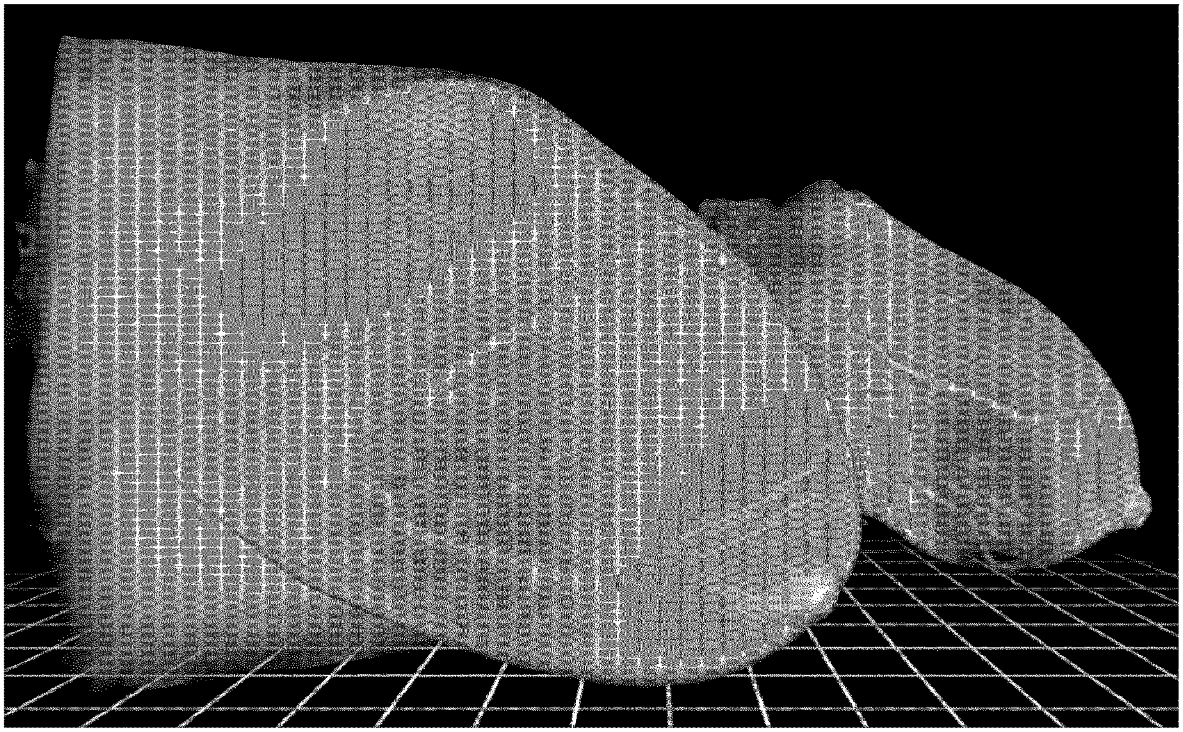
FIG. 2 shows an example of the second interface showing a 3D representation of a 3D image prior to the selection of pixels or voxels through annotations, FIG. 3 corresponds to FIG. 1, after updating the 2D representation of the 2D image on the basis of a semi-automatic definition or parametrization of a transfer function by selecting pixels or voxels through annotations, FIG. 4 corresponds to FIG. 2, after updating the 3D representation of the 3D image on the basis of said semi-automatic definition or parametrization of the corresponding transfer function.
Figure 3:
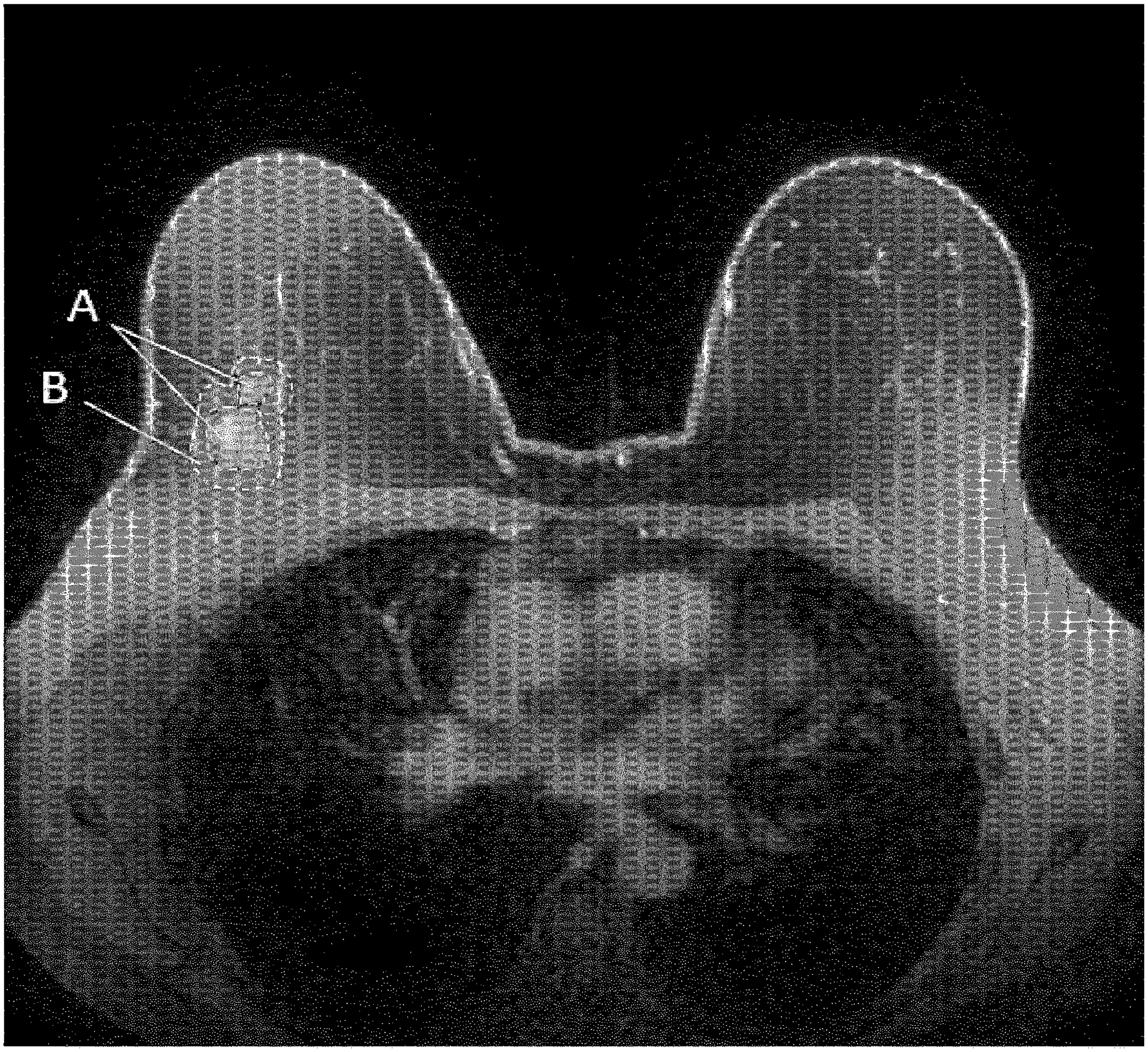
Figure 4:
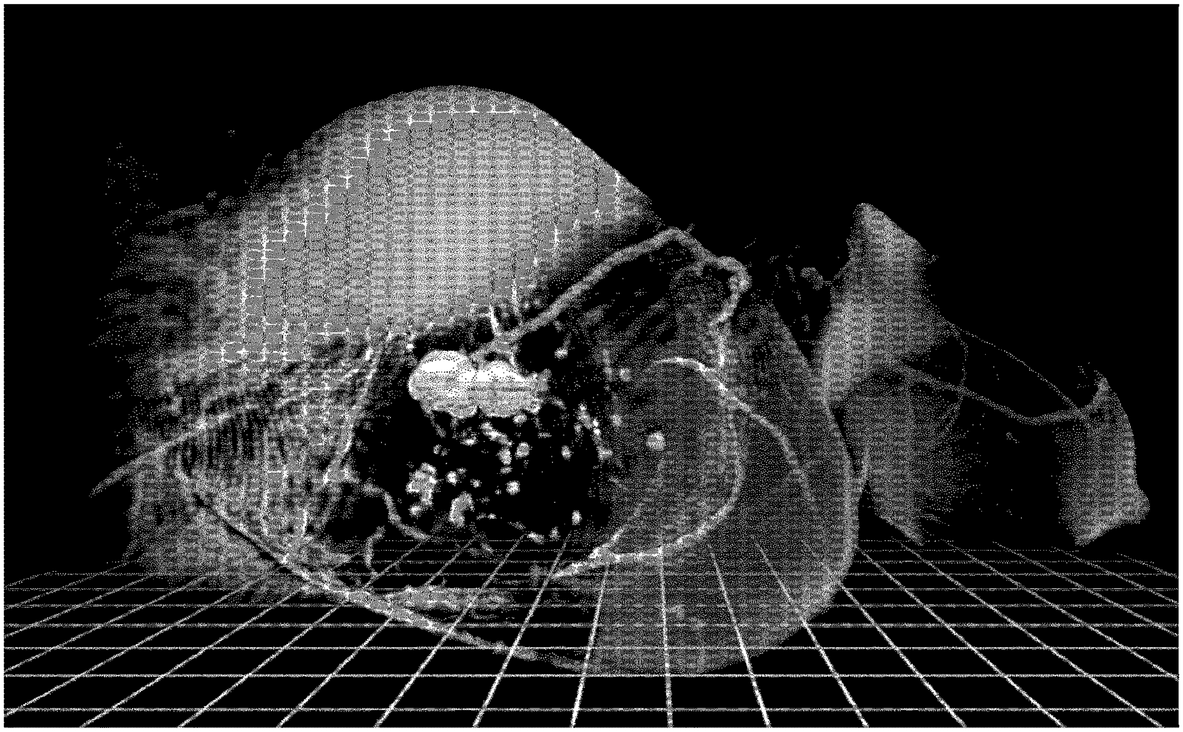

FIGS. 1 and 2 represent the first and second interface showing respectively a first or 2D representation of a 2D image of a specific zone of a patient and a second or 3D representation of a 3D image of said specific zone. The zone of interest in these figures is a breast cancer tumour situated in a patient's right breast. The tumour is clearly visible in the 2D interface representation, however to visualize the tumour in 3D requires an accurate parametrization of the transfer function. FIGS. 3 and 4 illustrate the same zones of the patient, after updating the transfer functions in said interfaces. The first and second domains of interest A and B are represented in FIG. 3. The letters and the lines (hatched lines and solid lines) designating said domains of interest A and B have been added in FIG. 3.

As mentioned above, said 2D and 3D images can be obtained through the same volumetric image data, which may be multi-channel. 2D image may be a slice-based image of said volumetric image.

In the first and/or the second interface, a first user (e.g. a radiologist) and a second user (e.g. a surgeon) are able to select a group of pixels or voxels onto said 2D and 3D representations, through annotations. Such selection can be created and modified by both users as the annotations are updated, visible and able to be modified in both interfaces and representations.

A transfer function can be calculated for each interface or for only one interface (for example for the second interface), on the basis of said selection.

The transfer function is defined to optimize an objective function $\mathcal{L}$. A transfer function is defined as a mapping $\Phi$: $V \rightarrow \mathcal{G}$ with V the space of pixel or voxel features and $\mathcal{G}$ a set of function space (that depends in nature in the application) in which two functions are defined: T(v) the transparency function and C(v) the colour mapping function, with $\upsilon$ the features associated to a pixel or a voxel.

In the below described embodiments or applications, we will define the objective function optimize $\mathcal{L}$ and the procedure to obtain (T, C).

In a first embodiment or application, a statistical test is used to define the transfer function. More particularly, said test rely on the Maximal Mean Discrepancy (MMD).

The following list of kernels is defined:

$$-k_G(x, x') = \sigma^2 \exp\left(-\frac{(x-x')^2}{2l^2}\right),$$

$$-k_{Per}(x, x') = \sigma^2 \exp\left(-2\frac{\sin^2\left(\frac{\pi(x-x')}{p}\right)}{l^2}\right),$$

$$-k_{lin}(x, x') = \sigma_b^2 + \sigma_v^2 (x-l)(x'-l)$$

$$-k_{cau}(x, x') = \sigma^2\left(1 + \frac{(x-x')^2}{2\alpha l^2}\right)^{-\alpha}$$

$$-k_{exp}(x, x') = \exp\left(-\left(\frac{r}{l}\right)^{\gamma}\right)$$

where:

- x and x' are features of the corresponding pixels or voxels—
- $\{\sigma, l, p, \sigma_b, \sigma_v, \alpha, \gamma\}$ are hyper-parameters of the kernels, these parameters being predefined, or set automatically or by the user.

The above mentioned hyperparameters may be modified or set by the user through at least one interface.

Maximum Mean Discrepancy relies in the notion of embedding probability measures in a Reproducing Kernel Hilbert Space (RKHS). Embedding probability measures is a generalization of kernel methods which deal with embedding points of an input space as elements in an RKHS.

We have a probability P and a continuous positive definite real-valued kernel k ($\mathcal{H}$ to be the corresponding RKHS) defined on a separable topological space $\xi$, P is embedded into $\mathcal{H}$ as $\mu_P = \int k(.,x)dP(x)$, called the kernel mean.

Based on the above embedding of P, we define a distance, the Maximum Mean Discrepancy (MMD), on the space of probability measures as the distance between the corresponding mean elements, i.e., $$MMD_k(P, Q) = \|\mu_P - \mu_{Q\mathcal{H}}\|$$

We define the regularised density the convolution of the histogram of features with the kernel K $(x, x') = k_G(x-x')$ as h(v)

While features can be adapted to specific application, common features associated to voxels for a stack $l$ are:

- the value of the pixel or voxel v,
- $\nabla_l v$ the regularised gradient (over scale l) of the pixel or voxel values, regularisation is performed by Gaussian convolution $\nabla_l v = \nabla(\mathcal{N}_l * I)$ with $\mathcal{N}$ the Gaussian of null averaged value and standard deviation of l and I is the image stack
- $S_l(v)$ the entropy of a patch of size l around pixel or voxel v,
- $d(v) = (\mathcal{N}_{l_1} * I)(v) - (\mathcal{N}_{l_2} * I)(v)$ difference of convoluted images at pixel or voxel v,
- where $(l_1, l_2)$ are the two scales associated to the Gaussian I is the image stack,
- $\sigma_l(v)$ the standard deviation of the patch of size l centred on pixel or voxel v,
- $KL_{l,m}(v)$ the Kullback-Liebler distance between the patch of size l and the surrounding patch of size l+m centred on pixel or voxel v,
- $\tilde{\mu}_l(v)$ the median values of the voxels in the patch of size l centred on pixel or voxel v,
- $\nabla \log(\mathcal{N}_l * I)$ the logarithmic derivative of the convolved image at pixel or voxel v,
- $d_{p\text{-}UMAP,l,m}(v)$ the low dimensional euclidean distance in the latent space generate by a parametric UMAP for a patch of size l and the surrounding patch of size l+m centred on pixel or voxel v. This feature is used on specialised solutions where a database of medical images has been assembled. A parametric UMAP has been trained on a predefined set of patches size on 2D image slices in the 3 main axes (Sagital, Coronal and Axial). The training has been done to reduce the dimension of the patch to a 2D latent space. When evaluating the distance l and l+m are approximated as the closest value used for training.
- $(r, \theta)_{p\text{-}UMAP}(v)$ the polar coordinates of the pixel or voxel v on the latent space generate by a parametric UMAP centres on pixel or voxel v,
- $S_{p\text{-}UMAP,l}(v)$ the convex hull surface of the domain of size l around pixel v Depending on the expected runtime the features are evaluated in the 2D image or slice of interest (the slice where the radiologist decided to annotate the data) or full volumetric 3D image. It does not lead to change in the following algorithm.

At least one of the transfer function is calculated according to the following steps:

selecting a first and a second domain of interest A and B, each domain comprising a group of pixels or voxels based on said selected pixels, creating a first feature tensor $v_A$ and a second feature tensor $v_B$ on the basis of pixels or voxels of the first and second domains of interest A and B, respectively. Each feature tensor $v_A$ or $v_B$ defines, for each pixel of the corresponding domain of interest A or B, at least one feature value selected from the above mentioned list of features. If a 16 bits graphics card is used, the total number of features of both feature tensor $v_A$ or $v_B$ may be up to 4 features. If a 32 bits graphics card is used, the total number of features of both feature tensor $v_A$ or $v_B$ may be up to 8 features.

$v_A$ or $v_B$ have respective size of $(n_A, m_A)$ and $(n_B, m_B)$ where $n_A$ is the number of pixel or voxels of the domain A $m_A$ is the number of features of each pixel or voxel of the domain A $n_B$ is the number of pixel or voxels of the domain B $m_B$ is the number of features of each pixel or voxel of the domain B $n_A$ may be different from $n_B$ and $m_A$ may be different from $m_B$.

depending on machine limitation, defining $n_{max}$, maximal number of pixels or voxels (A and B) to be considered choosing one kernel from the above predefined list of kernels and computing optimal MMD test to differentiate A and B using the following definition and equation:

We have the witness function $f^*(v) \propto \mu_P - \mu_Q$ and $$\hat{\mu}_P = \frac{1}{n}\sum_i \phi(x_i)$$

the empirical feature mean for P:

$\phi(x)=[\ldots \phi_i(x) \ldots]$ is the feature map $\phi(x) \in \mathcal{F}$, $k(x,x') = \langle \phi(x), \phi(x') \rangle_{\mathcal{F}}$ and $\mathcal{F}$ the class of functions.

defining, for each pixel or voxel of the image, the colour C of said pixel or voxel with the following equation:

where $f^*(v)$ is the witness function of the value of the pixel or voxel v, defined by $$f^*(v) \propto \mu_P - \mu_Q = \frac{1}{m}\sum_{i=1}^{m} k(x_i, v) - \frac{1}{n}\sum_{j=1}^{n} k(y_j, v)$$

where k is a kernel defining a value representative of the distance between the features associated to pixel or voxel $x_i$ belonging to domain A and $y_j$ and the features associated to the pixel or voxel v, with m the number of pixel or voxel in A and n the number of pixel or voxel in domain B, computing the colour C and T defined by the following equations:

$$T(v) = \frac{h_A(v) + h_B(v)}{z_{A,B}} \quad C(v) = \frac{f^*(v) - \min(f^*(v))}{\max(f^*(v)) - \min(f^*(v))}$$

where:

$h_A(v)=(k*\rho)(v)$ is the smoothed density, convolution of the kernel with the density of features, of the features associated to voxel v of the first domain A with the kernel k, $h_B(v)=(k*\rho)(v)$ is the smoothed density, convolution of the kernel with the density of features, of the features associated to voxel v of the second domain B with the kernel k, and $Z_{A,B}$ is a normalising constant ensuring that $\max(Z_{A,B})=c$ with $c \leq 1$ a predetermined constant defining the maximal transparency factor.

In a second embodiment or application, a probability distribution over features is used to define the transfer function.

The algorithm defines the colour of pixel or voxel from the product of a feature of interest and the shifted probability of the voxel to belong to one of the structure (A, B) performed by one shot learning.

Here, the learning is performed only on the data the radiologist and surgeons are working on. Learning is not performed from a dataset. Some features used for the one shot learning can be derived from inferences trained on specific datasets.

The following list of kernels is defined:

$$-k_G(x, x') = \sigma^2 \exp\left(-\frac{(x - x')^2}{2l^2}\right),$$

$$-k_{Per}(x, x') = \sigma^2 \exp\left(-2\frac{\sin^2\left(\frac{\pi(x - x')}{p}\right)}{l^2}\right),$$

$$-k_{lin}(x, x') = \sigma_b^2 + \sigma_v^2(x - l)(x' - l)$$

$$-k_{cau}(x, x') = \sigma^2\left(1 + \frac{(x - x')^2}{2\alpha l^2}\right)^{-\alpha}$$

$$-k_{exp}(x, x') = \exp\left(-\left(\frac{r}{l}\right)^{\gamma}\right)$$

We define the binary classifier using a Gaussian process. We associate to the domain A the "label" y=+1 and to the domain B the "label" y=−1. We define the latent variables $f(v)$ and the logistics function $\pi(v)=p(y=+1|v)=\mathcal{S}(f(v))$ With $\mathcal{S}$ the logistic function. We define V the set of tagged pixels or voxels (corresponding to domains (A, B) in the following)

We have for a pixel or voxel $v_*$ $$\pi(v_*) = \pi_*(y_* = +1|V, y, v_*) = \int \mathcal{S}(f_*)p(f_*|V, y, v_*)df_* \text{ with}$$

$$p(f_*|V, y, v_*) \int p(f_*|V, y, v_*)p(f|V, y)df \; p(f|V, y) = \frac{p(y|f)p(f|V)}{p(y|f)}$$

where

At least one of the transfer function is calculated according to the following steps:

selecting a first and a second domain of interest A and B, each domain comprising a group of pixels or voxels based on said selected pixels, defining on the computing platform the maximal number of pixels or voxels $n_{max}$ that can be used on the procedure defining the list of features of interest $\{\ldots g_i(v) \ldots\}$ creating a first feature tensor $v_A$ and a second feature tensor $v_B$ on the basis of pixels or voxels of the first and second domains of interest A and B, respectively. Each feature tensor $v_A$ or $v_B$ defines, for each pixel of the corresponding domain of interest A or B, at least one feature value selected from the above mentioned list of features for the first embodiment or application.

$v_A$ or $v_B$ have respective size of ($n_A$, $m_A$) and ($n_B$, $m_B$) where $n_A$ is the number of pixel or voxels of the domain A $m_A$ is the number of features of each pixel or voxel of the domain A $n_B$ is the number of pixel or voxels of the domain B $m_B$ is the number of features of each pixel or voxel of the domain B $n_A$ may be different from ng and my may be different from $m_B$.

sampling voxels or pixels for (A, B) to have $$n_A^* = n_B^* \text{ and } 2n_A^* = n \leq n_{max}$$

where:

$$n_A^*$$

is the number of pixels or voxels sampled in the domain A $$n_B^*$$

is the number of pixels or voxels sampled in the domain B defining a classifier as a binary Gaussian process classifier (P, π)

computing Laplace approximation computing the colour C and T defined by the following equations:

$$C(v) = \frac{f^*(v) - \min(f^*(v))}{\max(f^*(v)) - \min(f^*(v))} \text{ with } f^*(v) = (\beta p_A(v) + 1)g(v)$$

as the normalized product of the shifted probability for said pixel or voxel to belong to domain A by the value of one feature, g(v) of said pixel or voxel v. β is a predefined constant.

$$T(v) = \frac{h_A(v) + h_B(v)}{z_{A,B}}$$

where:

$h_A(v)=(k*\rho)(v)$ is the smoothed density, convolution of the kernel with the density of features, of the features associated to voxel v of the first domain A with the kernel k, $h_B(v)=(k*\rho)(v)$ is the smoothed density, convolution of the kernel with the density of features, of the features associated to voxel v of the second domain B with the kernel k, and $Z_{A,B}$ is a normalising constant ensuring that $\max(Z_{A,B})=c$ with $c \leq 1$ a predetermined constant defining the maximal transparency factor.

In the software implementation the above mentioned procedure is run for the set of kernels defined above. Within at least one interface, the corresponding user can change the kernel. By default, the kernel $k_G$ may be displayed.

Such Bayesian approach allows better generalisations of the result if the pixels or voxels tagged are in very small numbers. If there are numerous tagged pixels or voxels, MMD (first embodiment or application) will allow faster calculations and higher efficiency than the Bayesian approach (second embodiment or application).

We claim:

1. A method implemented by computer for visualizing a zone of an object in an interface, said method comprises the following steps:

obtaining at least one image of said zone, said image comprising at least one channel, said image being a 2-dimensional or 3-dimensional image comprising pixels or voxels, respectively, a value being associated to each channel of each pixel or voxel, a representation of said image being displayed in the interface, said representation comprising a color and a transparency for each of said pixels or voxels, obtaining at least one annotation from a user, said annotation defining a group of selected pixels or voxels of said image, calculating a transfer function based on said group of selected pixels or voxels of the image, applying said transfer function to the values of each channel of the image, updating said representation of said image in the interface, the color and the transparency of said pixels or voxels of said representation being dependent on said transfer function, said transfer function being calculated by the steps comprising:

selecting a first domain of interest A and a second domain of interest B, each domain comprising a group of pixels or voxels based on said group of selected pixels, creating a first feature tensor based on said pixels or voxels of said first domain and a second feature tensor based on said pixels or voxels of said second domain, defining a statistical test that differentiates said first domain A from said second domain B through the optimate Maximum Mean Discrepancy (MMD) of statistics computed from said first domain A and statistics computed from said second domain B, defining, for each said pixel or voxel of said image, said color of each said pixel using the equation:

$$C(v) = \frac{f^*(v) - \min(f^*(v))}{\max(f^*(v)) - \min(f^*(v))}$$

where f*(v) is the witness function of said value of said pixel or voxel, v, defined by the equation:

$$f^*(v) \propto \mu_P - \mu_Q = \frac{1}{m}\sum_{i=1}^{m} k(x_i, v) - \frac{1}{n}\sum_{j=1}^{n} k(y_j, v)$$

wherein k is a kernel defining a value representative of a distance between pixel or voxel, $x_i$, from said first domain A or pixel or voxel, $y_j$ from said second domain, and the features associated to the pixel or voxel v, m defines the number of pixels or voxels in the first feature A, and n defines the number of pixels or voxels in the second feature B, defining for each of said pixels or voxels of the image, the transparency of said pixel or voxel with the equation:

$$T(v) = \frac{h_A(v) + h_B(v)}{z_{A,B}}$$

wherein $h_A(v)$ is the smoothed density resulting from the convolution of the kernel k with the density of features in said first domain A associated with pixel or voxel v, $h_B(v)$ is the smoothed density resulting from the convolution of the kernel k with the density of features in said second domain B associated with pixel or voxel v, and $Z_{A,B}$ is a normalizing constant that ensures that $\max(Z_{A,B})=c$ with $c \leq 1$.

2. The method of claim 1 further comprising:

obtaining a 2-dimensional or 2D image of said zone, said 2D image comprising pixels and a channel, a value being associated to each channel of each pixel of said 2-dimensional image, a representation of said 2D image being displayed in a first interface, obtaining a 3-dimensional or 3D image of said zone, said 3D image comprising voxels and a channel, a value being associated to each channel of each voxel of said 3D image, at least some of the voxels of the 3D image corresponding to some pixels of the 2D image, a representation of said 3D image being displayed in a second interface, obtaining at least one annotation from a user, said annotation defining a group of selected pixels of said 2D image or a group of selected voxels of said 3D image, propagating said group of selected pixels or voxels selected in the 2D or 3D image to the 3D or 2D image, respectively, by selecting the voxels or the pixels of said 3D or 2D image that corresponds to the group of selected pixels or voxels of said 2D or 3D image, respectively, calculating a first transfer function based on said group of selected pixels of said 2D image and applying said first transfer function to the values of each channel of the 2D image, updating the representation of the 2D image in the first interface, in which the color and the transparency of the pixels of said representation are dependent on the first transfer function, calculating a second transfer function based on said selected voxels of said 3D image and applying said second transfer function to the values of each channel of the 3D image, updating the representation of the 3D image in the second interface, in which the color and the transparency of the voxels of said representation are dependent on the second transfer function.

3. The method according to claim 1, wherein said group of selected pixels or voxels of the 2D or 3D image, respectively, is updated by obtaining an additional annotation from a user through the interface.

4. The method according to claim 1, wherein each feature tensor defines, for each pixel or voxel of the corresponding domain of interest, a feature value computed by a method chosen from the group consisting of:

the value of the pixel or voxel v, $\nabla_l v$, a regularised gradient (over scale l) of the pixel or voxel values, wherein regularisation is performed by Gaussian convolution $\nabla_l v=\nabla(\mathcal{N}_l * I)$ with $\mathcal{N}$ the Gaussian of null averaged value and standard deviation of l, $S_1(v)$, a computed entropy of a patch of size l around pixel or voxel v, $d(v)=(\mathcal{N}_{l_1} * I)(v)-(\mathcal{N}_{l_2} * I)(v)$, a difference of convoluted images at pixel or voxel v, where $(l_1, l_2)$ are two scales associated to the Gaussian and I is an image stack, $\sigma_l(v)$, a computed standard deviation of a patch of size l centred on pixel or voxel v, $KL_{l,m}(v)$, a computed Kullback-Liebler distance between a patch of size l and a surrounding patch of size l+m centred on pixel or voxel v, $\tilde{\mu}_l(v)$, a set of computed median values of the voxels in a patch of size l centred on pixel or voxel υ, $\nabla \log(\mathcal{N}_l * I)$ a logarithmic derivative of a convolved image at pixel or voxel υ, $d_{p\text{-}UMAP,l,m}(v)$ a low dimensional Euclidean distance in a latent space generated by a parametric UMAP for a patch of size l and a surrounding patch of size l+m centred on pixel or voxel v, $(r, \theta)_{p\text{-}UMAP}(v)$, polar coordinates of the pixel or voxel v on a latent space generated by a parametric UMAP centred on pixel or voxel v, and $S_{p\text{-}UMAP,l}(v)$, a convex hull surface of a domain of size l around pixel v.

5. The method of claim 1, wherein said kernel k is selected from the group consisting of:

$$-k_G(x, x') = \sigma^2 \exp\left(-\frac{(x-x')^2}{2l^2}\right),$$

$$-k_{Per}(x, x') = \sigma^2 \exp\left(-2\frac{\sin^2\left(\frac{\pi(x-x')}{p}\right)}{l^2}\right),$$

$$-k_{lin}(x, x') = \sigma_b^2 + \sigma_v^2 (x-l)(x'-l),$$

$$-k_{cau}(x, x') = \sigma^2\left(1 + \frac{(x-x')^2}{2\alpha l^2}\right)^{-\alpha}, \text{ and}$$

$$-k_{exp}(x, x') = \exp\left(-\left(\frac{r}{l}\right)^\gamma\right),$$

wherein x and x' are features of the corresponding pixels or voxels—

$\{\sigma, l, p, \sigma_b, \sigma_v, \alpha, \gamma\}$ are hyper-parameters of the kernels.

6. The method of claim 1, wherein an action generated on a first device is transmitted to a second device through a manager storing data in a memory, said data comprising a first representation comprising a parameter representative of said first action the first representation being updated on the basis of the stored data and the set of original images.

7. The method of claim 6, wherein each manager, being part of an application and further comprising a manager data storage, implements a function chosen from the list consisting of:

exporting data from the manager data storage to a format readable outside of the application, importing data from outside of the application to the manager data storage, receiving data from an interface and storing said data into the manager data storage and updating all other interfaces with a visual readout of this data inclusion, removing data from an interface and removing said data from the manager data storage and updating all other interfaces with a visual readout of this data removal, updating a visual readout of a given interface with the addition of a new visual element, and removing a visual readout of a given interface with the removal of an existing visual element.

8. The method of claim 7, further comprising a data element having a unique identifier to ensure synchronization between each interface.

9. The method of claim 1, wherein the representation of the 3D image is obtained through volume ray casting methods.

10. The method of claim 1, wherein the first interface is displayed on a computer screen and the second interface is displayed on a device chosen from the group consisting of: a computer screen, and on a display of a virtual reality device.

11. A computer-readable storage medium having stored thereon instructions which, when executed by a processor, cause the processor to perform the method of claim 1.

12. Computer device comprising:

an input configured for receiving an image of a zone of an object, a memory configured to store the instructions according to claim 11, a processor configured to access the memory for reading said instructions and executing said instructions, an interface for displaying the representation of an image obtained by executing said method.

13. The computer device of claim 12, wherein the interface is a first interface and is configured to display a representation of a 2D image, the computer device further comprising a second interface configured to display a representation of a 3D image.

14. The computer device of claim 12, wherein the first interface is displayed on a computer screen and the second interface is displayed on a device chosen from the group consisting of a computer screen and a virtual reality device.

15. A method of generating a 3D model of a patient's anatomical structure, the method comprising:

implementing by computer the method according to claim 1 on a medical 3D-image of an object wherein the object is a patient's anatomical structure(s) comprising a zone of medical interest and the medical 3D-image is chosen from the group consisting of: a magnetic image resonance (MRI) image, a Computed Tomography (CT) scan image, a Positron Emission Tomography (PET) scan image, and a numerically processed ultrasound recordings image, and displaying a 3D model of the patient's anatomical structure including the zone of medical interest.

16. The method of claim 15, wherein a user provides an annotation in the medical 3D-image wherein the annotation selects pixels or voxels in the zone of medical interest to improve visualization of said zone of medical interest, or visualization of the boundaries of the zone of medical interest, or the annotation selects pixels or voxels outside said zone of medical interest to enable image transformation by cropping or deletion of interfering structures.

17. The method according to claim 15, wherein the method performed on an image chosen from the group consisting of a raw 3D image imaging data, or a segmented 3D image data.

18. A method of analyzing a 3D model obtained from of a medical 3D-image previously acquired from a patient, the method comprising:

executing on a computer the method according to claim 1 on a medical 3D-image of an object wherein the object is a patient's anatomical structure comprising a zone of medical interest and the medical 3D-image is a magnetic image resonance (MRI) image, a Computed Tomography (CT) scan image, a Positron Emission Tomography (PET) scan image or a numerically processed ultrasound recordings image, displaying a 3D model of the patient's anatomical structure including the zone of medical interest, and analyzing the displayed 3D model, in particular, visualizing, tagging, manipulating and measuring metrics based on imaging data of the 3D model, thereby characterizing the patient's anatomical structure in the zone of medical interest.

19. A method of diagnosing or monitoring a patient's condition, disease or health status, the method comprising:

implementing the method of claim 18, collecting data relative to metrics measured based on imaging data wherein the metrics enable mapping morphological, geometrical or position features of medical interest for the patient's condition, disease or health status.

20. The method according to claim 19 for detection or monitoring of a tumor in a patient wherein the visualized or measured metrics are selected from the group consisting of localization of the tumor in a specific organ or part thereof, determination of a number of lesions, position of the tumor relative to the contours of an affected anatomical structure or body part and, in particular, an affected organ, determination of the volume of a tumor or of the ratio of volumes respectively of the tumor, and a residency volume of an affected organ.

* * * * *